United States Patent [19]

Ellison

[11] 4,407,277

[45] Oct. 4, 1983

[54] SURGICAL APPARATUS

[76] Inventor: Arthur E. Ellison, Adams Rd., Williamstown, Mass. 02167

[21] Appl. No.: 200,789

[22] Filed: Oct. 27, 1980

[51] Int. Cl.³ .............................................. A61F 13/00
[52] U.S. Cl. ...................................... 128/82; 128/327; 128/DIG. 15; 128/133; 128/134; 269/328
[58] Field of Search ..................... 128/133, 20, 82, 83, 128/84 R, 84 A–84 C, 87 C, 327, DIG. 15; 269/328

[56] References Cited

U.S. PATENT DOCUMENTS

| | | | |
|---|---|---|---|
| 1,136,397 | 4/1915 | Bloch. | |
| 1,880,945 | 10/1932 | Ettinger. | |
| 1,887,022 | 11/1932 | Hoffman et al. | 128/327 |
| 2,057,592 | 10/1936 | Raiford | 128/84 R |
| 2,091,643 | 8/1937 | Longfellow | 128/84 R |
| 2,266,231 | 12/1941 | Mazzeo et al. | 128/DIG. 6 |
| 2,357,323 | 9/1944 | Goldberg | 128/84 R |
| 2,477,562 | 8/1949 | Anderson | 128/84 B |
| 3,020,090 | 2/1962 | Stevens | 128/70 |
| 3,439,673 | 4/1969 | Sprecher | 128/133 |
| 3,625,210 | 12/1971 | Milkelson | 128/DIG. 6 |
| 3,717,144 | 2/1973 | Bimler | 128/80 |
| 3,753,557 | 8/1973 | Kelley | 269/328 |
| 3,802,692 | 4/1974 | Lipson | 269/325 |
| 3,888,243 | 6/1975 | Powlan | 128/84 C |
| 4,106,499 | 8/1978 | Ueda | 128/327 |
| 4,135,505 | 1/1979 | Day | 128/92 A |
| 4,181,297 | 1/1980 | Nichols | 269/328 |
| 4,299,213 | 11/1981 | Violet | 128/133 |

OTHER PUBLICATIONS

Arthroscopy Surgical Leg Brace, Advertising Brochure, E. W. Mfg., 1980.

Primary Examiner—Michael H. Thaler
Assistant Examiner—C. W. Shedd
Attorney, Agent, or Firm—Kenway & Jenney

[57] ABSTRACT

Apparatus for applying and maintaining forces and moments to the knee joint during arthroscopic surgery. The apparatus includes upper and lower leg restraining members which are rotatable and longitudinally movable with respect to each other and lockable in desired orientations to generate and maintain the forces and moments. Structure is also provided for applying lateral forces to the leg and for supporting instruments such as arthroscopes.

13 Claims, 5 Drawing Figures

SURGICAL APPARATUS

BACKGROUND OF THE INVENTION

Surgical procedures involving the knee joint are more difficult than many other surgical procedures because of the very small spaces in which to work inside the knee joint itself. Within the last few years the arthroscope, a small telescope designed to be inserted into the knee joint, has been developed to allow visualization within these small spaces. Initially, arthroscopes were used merely for diagnostic purposes. More recently, however, arthroscopes have been employed during the surgical procedure itself to permit improved visualization within the knee joint. It is even practical and beneficial to use more than one arthroscope during some surgical procedures on the knee joint. These arthroscopes may have different lenses and be positioned at different angles with respect to the knee joint as a further aid to the surgeon during the operation.

Obtaining the proper exposure of the knee joint during surgery is necessary for a successful result. Exposure required the opening up of the knee joint by the application of forces and moments which may even distort the joint thereby making the spaces within which the surgeon must work a bit larger. When surgery is performed under arthroscopic visualization, good exposure is essential not only to give the surgeon more room to perform the procedure but also to provide better visualization of the surgical field.

Heretofore, the opening up of the knee joint to provide the desired exposure was accomplished by an assistant who moved the knee through its various ranges of motion while applying considerable force to the knee joint. Stamina is required of such an assistant because knee operations often last for an hour or more; and strength is necessary because of the relative inelasticity of the ligaments supporting the knee joint. An inexperienced assistant, moreover, could actually make matters worse by not holding the knee joint steady enough to allow the surgeon to work expeditiously. When surgery was performed arthroscopically, the assistant supported the knee so as to open up the joint, and the surgeon held the arthroscope with one hand while performing the shaving, cutting or other procedure with his or her other hand.

At a later stage of development, the arthroscope was connected to a television camera so that the surgeon could view a monitor rather than looking through the device directly. In this situation, a second assistant was required to hold the arthroscope/camera combination and to move it according to the surgeon's instructions. Not only does the connection of arthroscopes to television cameras entail the cost of a second surgical assistant, but also, the television equipment itself is very expensive, so that only large medical centers can invest in such a system. Even with the use of a television system, the problem of maintaining the knee in the optimum position to provide good exposure remained unsolved.

It is, therefore, an object of the present invention to provide apparatus which not only applies and maintains forces and moments to the knee joint to provide the desired exposure, but which also is adapted to support one or more arthroscopes or other surgical implements in a preselectable and adjustable relation to the knee joint during surgery.

A further object of the invention is to provide such apparatus which is simple of construction and yet highly effective to provide the necessary exposure within which the surgeon can perform as compared with the capability of a human assistant.

Yet another object of this invention is apparatus which can apply and maintain forces and moments to the knee joint through all eight of its ranges of motion.

SUMMARY OF THE INVENTION

The apparatus for applying and maintaining in arbitrary directions forces and moments on a knee joint during surgical procedures according to the present invention comprises an upper leg restraining member adapted for immobilizing longitudinally and rotationally the upper leg and a lower leg restraining member adapted for immobilizing the lower leg. A structural assembly interconnects the upper leg restraining member and the lower leg restraining member. This structural assembly is adapted for establishing and preserving an arbitrary relative orientation between the upper leg restraining member and the lower leg restraining member so as to generate on the knee joint forces and moments in arbitrary directions. The interconnecting structural assembly also includes apparatus located intermediate the upper leg restraining member and the lower leg restraining member adapted for applying lateral forces to the upper leg. An instrument holding system which cooperates with and is supported by the interconnecting structural assembly is provided to hold surgical instruments in adjustable relation with respect to the knee joint.

In a preferred embodiment, the upper leg restraining member includes an inflatable tourniquet adapted to encircle the upper leg in close fitting, restraining relation when it is inflated. This tourniquet has an outer surface which includes a first gripping material. This gripping material is adapted for mating with a second gripping material which lines the inner surface of a rigid structure which encircles at least partially the outer surface of the tourniquet. In this way the tourniquet is fixed longitudinally and rotationally with respect to the rigid structure. In this embodiment a first lockable universal joint is provided for connecting the rigid structure of the upper leg restraining member to the interconnecting structural assembly, and a second lockable universal joint connects the lower leg restraining member to the interconnecting structural assembly. The interconnecting structural assembly itself includes a first arm to be attached to the upper leg restraining member and a second arm adapted for attachment to the lower leg restraining member. The first arm and second arm are mounted for adjustment and subsequent fixation of the separation between the two leg restraining members. A compression plate contoured to conform generally to the shape of the upper leg is provided for applying lateral forces to the upper leg. This compression plate includes a threaded shaft adapted for attachment to the interconnecting structural assembly so that its lateral position can be adjusted conveniently. For arthroscopic surgery on the knee joint, the interconnecting structural assembly also includes apparatus for supporting an arthroscope so that it may assume an arbitrary spatial relationship with respect to the knee joint during surgery.

The preferred apparatus for applying lateral forces to the upper leg with the above-mentioned compression plate includes a mounting block which is attached to the interconnecting structural assembly so that its longitudinal position thereon may be set as desired. This mounting block has an internal groove into which a height adjusting block slidably fits. This height adjusting block has a threaded hole adapted for receiving the threaded shaft of the compression plate.

In yet another embodiment of this invention a hydraulic system is provided for establishing and preserving the arbitrary relative orientation between the upper leg restraining member and the lower leg restraining member. The apparatus for applying lateral forces to the upper leg is also operated hydraulically in this embodiment. An attachment may be added that rigidly fixes the frame to the operating table.

BRIEF DESCRIPTION OF THE DRAWINGS

The invention disclosed herein will be understood better with reference to the following description and drawings in which.

DESCRIPTION OF THE PREFERRED EMBODIMENT

Figure 1:
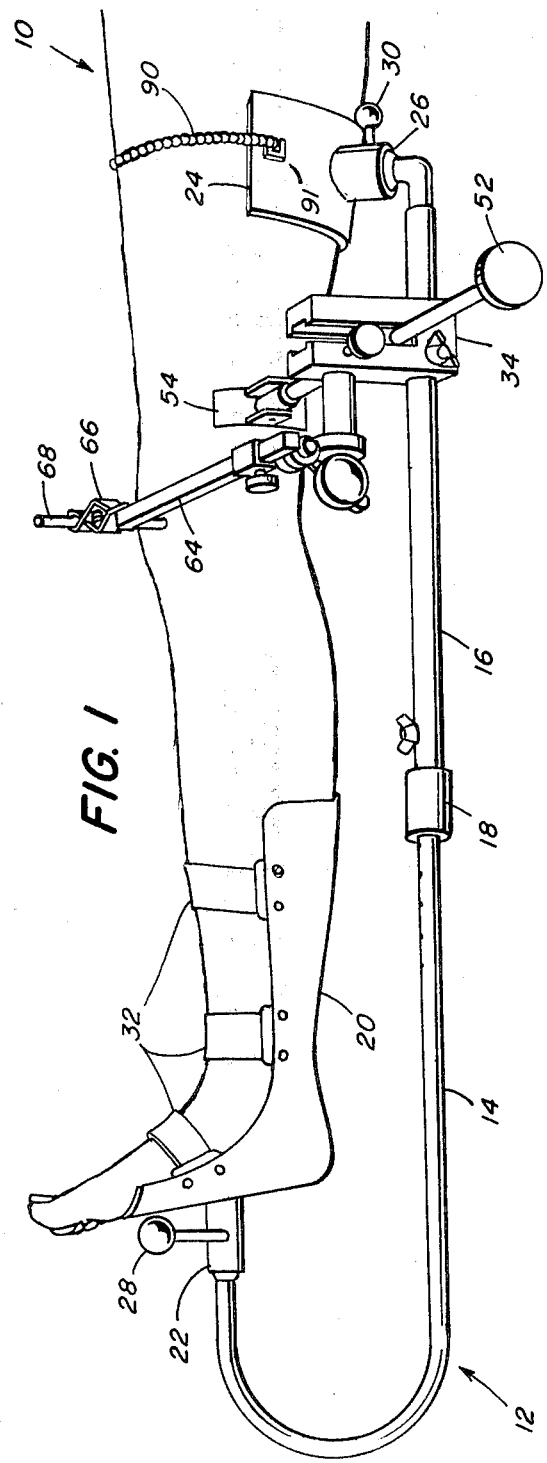
FIG. 1 is a schematic representation of the apparatus disclosed herein.

The same reference numbers will be used to identify corresponding elements throughout the several figures of the drawing.

Figure 2:
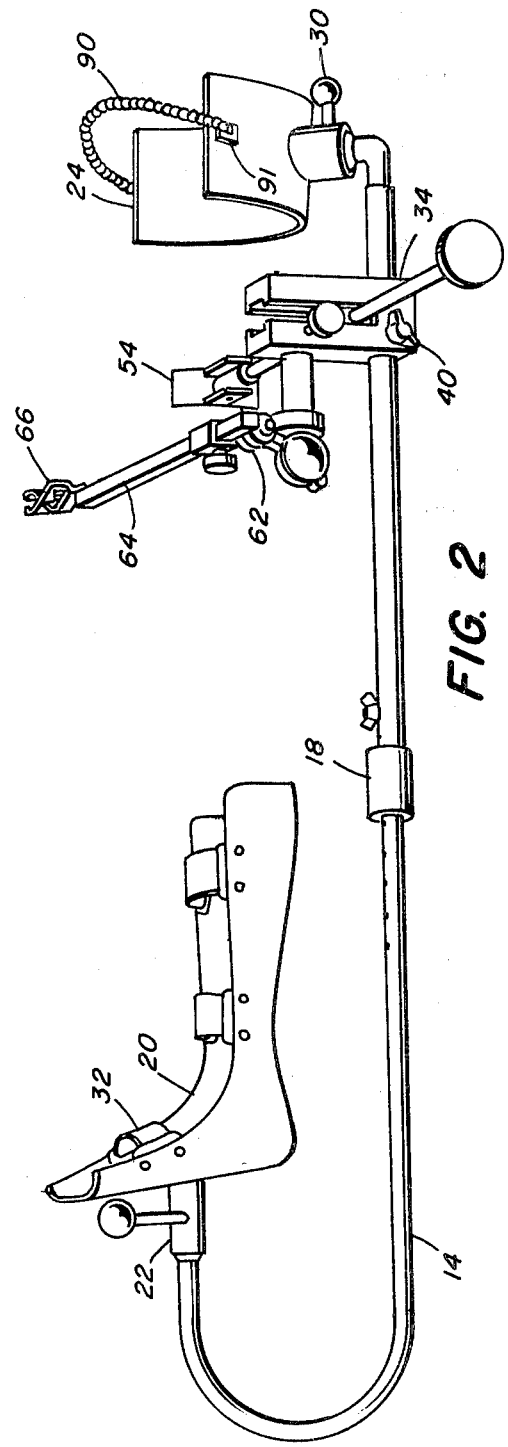
FIG. 2 is a perspective view of the apparatus.

With reference first to FIG. 1, a leg 10 is shown supported within a supporting structure indicated generally at 12. The supporting structure 12 comprises a first arm 14 slidingly mounted within a second arm 16. The relative longitudinal position of the first arm 14 with respect to the second arm 16 is fixable by means of a quick lock assembly 18. Referring now both to FIGS. 1 and 2, the first arm 14 supports a lower leg restraining member 20 through a universal locking joint 22. The second arm 16 supports an upper leg restraining member 24 by means of universal locking joint 26. The universal joints 22 and 26 of conventional design permit arbitrary rotations and then may be locked in a desired orientation by means of the levers 28 and 30.

The lower leg restraining member 20 is generally contoured to fit and support the foot and lower leg. Straps 32, preferably made of a VELCRO gripping material, are provided for rigidly restraining the foot and lower leg in the restraining member 20 so as substantially to prevent both longitudinal and rotational movement of the lower leg with respect to the restraining member 20. The upper leg restraining member 24 will be described in more detail below.

Figure 3:
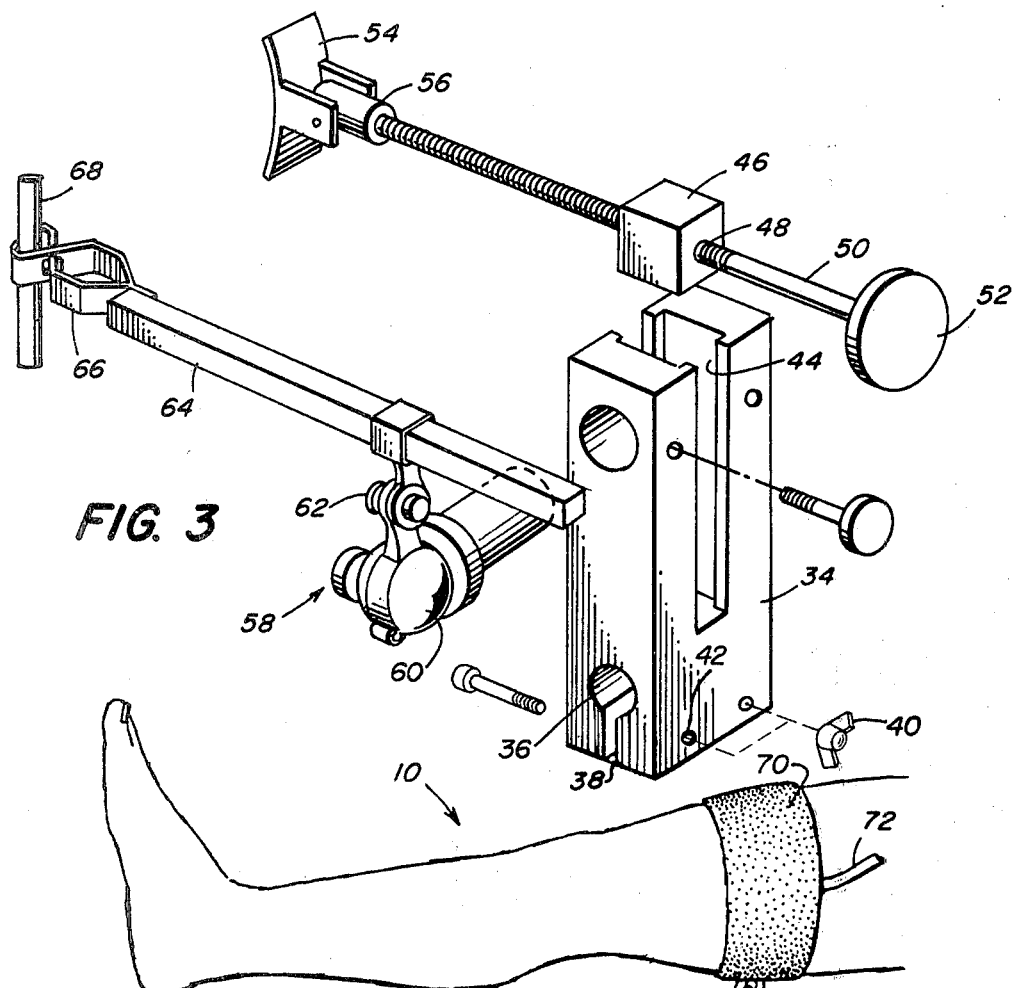
FIG. 3 is a perspective view of the assembly for applying lateral stress to the upper leg.

The way in which lateral forces are applied to the upper leg will be described with reference to FIGS. 1, 2 and 3. A mounting block 34 is supported on the arm 16. The block 34 includes a circular opening 36 sized for slidingly engaging the arm 16. A groove 38 extends the full length of the lower portion of the mounting block 34 so that the block 34 may be rigidly secured to the arm 16 at a desired location when wing nuts 40 are screwed into mating bolts (unnumbered) at the holes 42. Both the longitudinal position of the mounting block on the arm 16 may be adjusted as well as its rotational orientation. The mounting block 34 includes a groove 44 into which slidingly fits a height adjusting block 46. The height adjusting block 46 includes a threaded hole 48 adapted for receiving a threaded shaft 50. The shaft 50 includes a knob 52 on one end so that the shaft 50 may be turned by hand. The other end of the shaft 50 carries a compression plate 54 mounted on the shaft 50 through a universal joint 56. The compression plate 54 is approximately three inches wide and eight inches in extent along its curved portion.

The mounting block 34 is further adapted for carrying an instrument holding assembly represented generally at 58. The assembly 58 comprises a supporting member 60 which attaches the mounting block 34. The member 60 includes a lockable universal joint 62 which supports and permits an instrument holding arm 64 to be positioned and fixed in arbitrarily selected orientations. The distal end of the instrument holding arm 64 includes a spring activated grasping mechanism 66 adapted for holding surgical instruments, such as an arthroscope 68 depicted diagrammatically in FIG. 3. With this arrangement, the arthroscope 68 may be positioned arbitrarily with respect to the knee joint during a surgical procedure. It should be noted that the grasping mechanism 66 may also be used for holding other instruments such as probes, or a second arthroscope for obtaining a different visual perspective within the knee joint.

Figure 4:
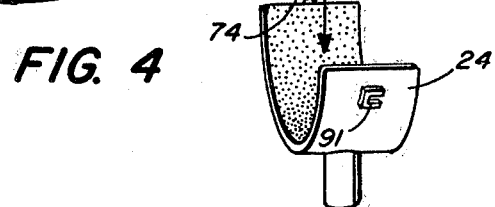
FIG. 4 is a schematic representation of the inflatable tourniquet and its mating rigid structure.

In order that the supporting structure 12 disclosed herein be able to apply forces and moments to stress the knee joint along any of its eight degrees of freedom to open the knee joint it is necessary that the upper leg be held substantially stationary both longitudinally and rotationally within the member 24. The novel method for so supporting the upper leg will now be described with the aid of FIG. 4. Shown in FIG. 4 is an upper leg encircled by an inflatable tourniquet 70. The tourniquet 70 is adapted for tightly encircling the upper leg and then is inflated through an inflation tube 72 so that even an upper leg having an excess of fat is maintained substantially fixed with respect to the tourniquet 70. The outer surface of the tourniquet 70 includes a hook and loop gripping material 74, such as VELCRO. The inner surface of the upper leg supporting member 24 is likewise covered with a mating gripping material, preferably VELCRO. Thus, when the upper leg supporting member 24 engages the tourniquet 70, the tourniquet 70 is fixed both longitudinally and rotationally with respect to the member 24. Moreover, because the inflatable tourniquet 70 very rigidly holds the upper leg, it is thus immobilized with respect to the upper leg supporting member 24. After the tourniquet-encased upper leg is placed into the member 24, it may be secured as by a chain 90 (FIG. 1) which prevents the member 24 from expanding under the pressure of the inflatable tourniquet. One end of the chain 90 is fixed as by welding to the member 24 and the other end is adapted to be locked in place by means of a slot or catch indicated at 91.

To perform a surgical procedure on the knee joint using the apparatus disclosed herein, the leg 10 is first secured within the lower leg restraining member 20 and the upper leg restraining member 24. These two members are then rotated so that the desired forces and moments are applied to the knee joint providing the proper exposure for the surgical procedure to be performed. Once the desired orientation is achieved the universal joints 22 and 26 are locked by means of their respective locking levers 28 and 30. If necessary or desired, the compression plate 54 is pressed against the leg 10 just above the knee by rotating the handle 52. In this way additional transverse forces may be applied to the knee joint. The next step is the proper positioning of the arthroscope 68 to allow observation within the knee joint. Thus the surgeon has both hands free because the arthroscope is rigidly fixed with respect to the knee joint, and the apparatus 12 produces the desired forces and moments on the knee joint to provide the exposure needed for a successful and expeditious surgical procedure.

Figure 5:
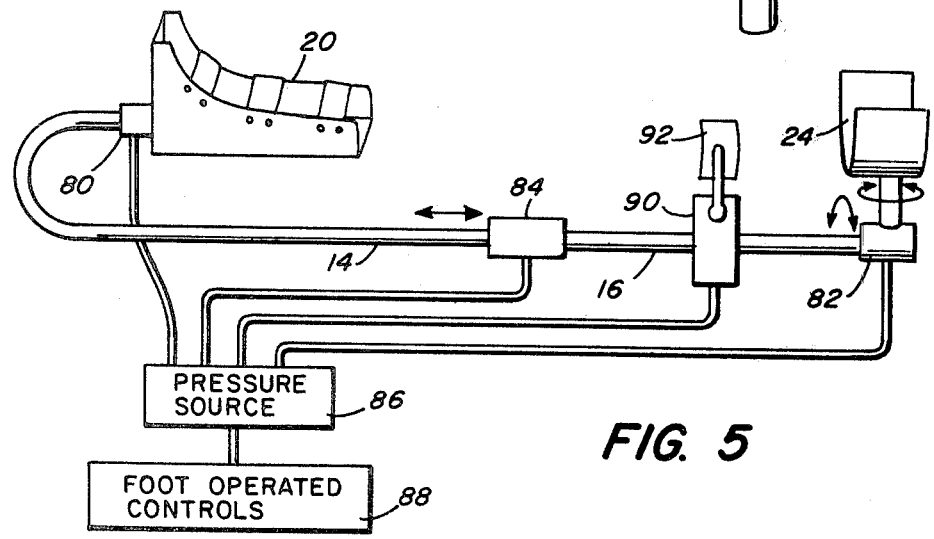
FIG. 5 is a schematic representation of an embodiment of this invention operated by hydraulic means.

Another embodiment of the invention is illustrated schematically in FIG. 5. In this embodiment, both the lower leg restraining member 20 and the upper leg restraining member 24 are attached to the arms 14 and 16 respectively through hydraulic universal actuators 80 and 82. In addition, the separation between the lower leg restraining member 20 and the upper leg restraining member 24 is controlled by linearly acting hydraulic actuator 84. The hydraulic actuators 80, 82 and 84 are connected to a source of pressurized hydraulic fluid 86. The pressure source 86 is in turn controlled by a set of foot operated controls 88. By means of the controls 88 the surgeon can actuate independently the hydraulic actuators 80, 82 and 84 so as to produce the desired forces and moments on a knee joint. In addition, another hydraulic actuator 90 may be provided for moving a thigh compression plate 92 into contact with the upper leg above the knee joint for providing transverse forces.

Rotatable upper and lower leg restraining members supported for adjustment of their separation in combination with a compression plate for applying lateral forces, results in apparatus capable of stressing the knee joint in all of its degrees of freedom. The knee joint has eight such degrees of freedom or ranges of motion, namely the four pairs: (1) traction and distraction or compression, (2) internal and external rotation, (3) flexion and extension, and (4) abduction and adduction (also known as valgus and varus). It is thus seen that the objects of this invention have been achieved in that there has been disclosed novel apparatus for applying these forces and moments to a knee joint in arbitrary directions so that the desired exposure of the knee joint may be obtained and preserved during a surgical procedure on the knee joint. In addition, the apparatus supports an arthroscope so that the surgeon has both hands free to perform the surgical procedure.

It is recognized that modifications and variations of this invention will occur to those skilled in the art, and it is intended that all such modifications and variations be included within the scope of the appended claims. In particular, it is to be understood that the apparatus disclosed herein may be atttached securely to an operating table, such attachment enhancing the rigidity with which the leg is held.

What is claimed is:

1. Apparatus for applying and maintaining forces and moments on a knee joint along any one or combination of its degrees of freedom to open said joint during arthroscopic surgical procedures on said knee joint comprising:
   an upper leg restraining member adapted for immobilizing longitudinally and rotationally said upper leg;
   a lower leg restraining member adapted for immobilizing longitudinally and rotationally said lower leg; and
   structural means interconnecting said upper leg restraining member and said lower leg restraining member;
   an arthroscope; and
   means for attaching said arthroscope to said interconnecting structural means to support said arthroscope in adjustable relation to said knee joint;
   said interconnecting structural means adapted for establishing and preserving a relative orientation between said upper leg restraining member and said lower leg restraining member and thereby generating said forces and moments on said knee joint along any one or combination of its said degrees of freedom to open up said knee joint for arthroscopic visualization.

2. The apparatus of claim 1 wherein said interconnecting structural means includes means located intermediate said upper leg restraining member and said lower leg restraining member adapted for applying lateral forces to said upper leg.

3. The apparatus of claim 2 wherein said means for applying said lateral force comprises a compression plate contoured to conform generally to the shape of said upper leg, said compression plate including a threaded shaft for mounting to said interconnecting structural means for adjusting its lateral position relative thereto.

4. The apparatus of claim 3 further including:
   a mounting block adapted for attachment to said interconnecting structural means, said mounting block having an internal groove;
   a height adjusting block slidably engageable within said groove;
   said height adjusting block adapted for receiving said threaded shaft.

5. The apparatus of claim 1 including instrument holding means cooperating with and supported by said interconnecting means so as to hold surgical instruments adjustably with respect to said knee joint.

6. The apparatus of claim 1 including a first lockable universal joint connecting said upper leg restraining member to said interconnecting structural means.

7. The apparatus of claim 1 including a second lockable universal joint connecting said lower leg restraining member to said interconnecting structural means.

8. The apparatus of claim 1 wherein said interconnecting structural means comprises a first arm adapted for attachment to said upper leg restraining member and a second arm adapted for attachment to said lower leg restraining member, said first arm and said second arm mounted for adjustment and fixation of the separation between said upper leg restraining member and said lower leg restraining member.

9. Apparatus for applying and maintaining forces and moments on a knee joint along anyone or combination of its degrees of freedom to open said joint during arthroscopic surgery on said knee joint comprising:
   an upper leg restraining member adapted for immobilizing longitudinally and rotationally said upper leg;
   a lower leg restraining member adapted for immobilizing longitudinally and rotationally said lower leg;
   structural means interconnecting said upper leg restraining member and said lower leg restraining member;
   said interconnecting structural means adapted for establishing and preserving a relative orientation between said upper leg restraining member and said lower leg restraining member thereby to generate said forces and moments on said knee joint along anyone or combination of its said degrees of freedom;

an arthroscope; and means for attaching said arthroscope to said interconnecting structural means to support said arthroscope in adjustable relation to said knee joint; whereby said knee joint is opened up for arthroscopic visualization by said applied forces and moments.

10. Apparatus for applying and maintaining forces and moments on a knee joint along any one on or combination of its eight ranges of motion during arthroscopic surgical procedures on said knee joint comprising:

an upper leg restraining member adapted for immobilizing longitudinaly and rotationally an upper leg;

a lower leg restraining member adapted for immobilizing longitudinally and rotationally said lower leg; and structural means interconnecting said upper leg restraining member and said lower leg restraining member, an arthroscope; and means for attaching said arthroscope to said interconnecting structural means to support said arthroscope in adjustable relation to said knee joint;

said interconnecting structural means adapted for establishing and preserving a relative orientation between said upper leg restraining member and said lower leg restraining member and thereby generating said forces and moments on said knee joint along anyone or combination of its said eight ranges of motion to open up said knee joint for arthroscopic visualization.

11. Apparatus for applying forces and moments to open a knee jont during surgery comprising:

an upper leg restraining member and a lower leg restraining member, said members being rotatable and longitudinally movable with respect to each other; and means for locking said members in desired orientations to generate and maintain said forces and moments that open said knee joint wherein said upper leg restraining member comprises in combination:

an inflatable tourniquet adapted to encircle said upper leg in close fitting, restraining relation when said tourniquet is inflated, said tourniquet including an outer surface of a first gripping material; and a rigid structure adapted for encircling at least partially the outer surface of said tourniquet, the inner surface of said rigid structure including a second gripping material adapted to mate with said first gripping material to fix longitudinally and rotationally said tourniquet with respect to said rigid structure.

12. The apparatus of claim 11 wherein said first and second gripping mmaterials are VELCRO.

13. Apparatus for applying and maintaining, in appropriate directions, forces and moments to open a knee joint during surgical procedures on said knee joint commprising:

an upper leg restraining member adapted for immobilizing longitudinally and rotationally said upper leg;

a lower leg restraining member adapted for immobilizing longitudinally and rotationally said lower leg; and structural means interconnecting said upper leg restraining member and said lower leg restraining member, said interconnecting structural means adapted for establishing and preserving a relative orientation between said upper leg restraining member and said lower leg restraining member and thereby generating said forces and moments in desired directions on said knee joint so as to open same for arthroscopic visualization and wherein said upper leg restraining member comprises in combination:

an inflatable tourniquet adapted to encircle said upper leg in close fitting, restraining relation when said tourniquet is inflated, said tourniquet including an outer surface of a first gripping material; and a rigid structure adapted for encircling at least partially the outer surface of said tourniquet, the inner surface of said rigid structure including a second gripping material adapted to mate with said first gripping material to fix longitudinally and rotationally said tourniquet with respect to said rigid structure.

* * * * *